(12) United States Patent
Lau (10) Patent No.: US 7,951,576 B2
(45) Date of Patent: May 31, 2011

(54) METHODS FOR PREPARING CELLS AND VIRUSES

(75) Inventor: David Lau, Wayland, MA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 172 days.

(21) Appl. No.: 11/718,455

(22) PCT Filed: Nov. 4, 2005

(86) PCT No.: PCT/US2005/040170
§ 371 (c)(1),
(2), (4) Date: Apr. 21, 2008

(87) PCT Pub. No.: WO2006/052826
PCT Pub. Date: May 18, 2006

(65) Prior Publication Data
US 2008/0318301 A1    Dec. 25, 2008

Related U.S. Application Data

(60) Provisional application No. 60/625,321, filed on Nov. 5, 2004.

(51) Int. Cl.
*C12N 15/85* (2006.01)
*C12N 7/00* (2006.01)

(52) U.S. Cl. ......... 435/235.1; 435/363; 435/2; 435/455; 424/232.1

(58) Field of Classification Search .................. None
See application file for complete search history.

(56) References Cited

U.S. PATENT DOCUMENTS 5,698,433 A * 12/1997 Kistner et al. .............. 435/239

FOREIGN PATENT DOCUMENTS

| EP | 0855441 A2 | 7/1998 |
|---|---|---|
| WO | WO03/054175 A1 * | 7/2003 |
| WO | WO03/076462 A1 * | 9/2003 |
| WO | WO03/097846 A1 * | 11/2003 |

OTHER PUBLICATIONS

Diamandopoulos et al. Am. J. Pathol. 1969, vol. 56(1), pp. 59-77.*
Earl et al. Preparation of cell cultures and vaccinia virus stocks in Unit 5.12 of Current Protocols in Protein Science, published 2003, pp. 1-9.*
Pendola et al. Cancer Resarch 1973, vol. 33, pp. 351-355.*
Hoffman et al. "Rapid isolation of the choriocapillary endothelial cells by lycopersicon esculentum-coated dynabeads," Graefe's Archive for Clinical and Experimental Ophthalmology, vol. 236, No. 10, 779-784, 1998.
Takemoto et al. "A new method for large scale isolation of kidney glomeruli from mice," American Journal of Pathology, vol. 161, No. 3, 799-805, Sep. 2002.
Kim Jin Nam et al. "Enriched gonadal migration of donor-derived gonadal primordial germ cells by immunomagnetic cell sorting in birds," Molecular Reproduction and Development, vol. 68, No. 1, 81-87, May 2004.
Butowt et al. "Purification of chick retinal ganglion cells for molecular analysis: Combining retrograde labeling and immunopanning yields 100% purity," Journal of Neuroscience Methods, vol. 95, No. 1, 29-38, Jan. 31, 2000.
Silim et al. "A simple technique for preparation of chicken embryo skin cell cultures," Avian Diseases, American Association of Avian Pathologists, vol. 26, No. 1, 182-185, 1982.
Drexler et al., "Highly attenuated modified vaccinia virus Ankara replicates in baby hamster kidney cells, a potential host for virus propagation, but not in various human transformed and primary cells," *Journal of General Virology*, 79, 347-352 (1998).
Hornemann et al., "Replication of Modified Vaccinia Virus Ankara in Primary Chicken Embryo Fibroblasts Requires Expression of the Interferon Resistance Gene E3L," *Journal of Virology*, 77 (15), 8394-8407 (2003).
Roberts, "Efficient removal of viruses by a novel polyvinylidene fluoried membrane filter," *Journal of Virological Methods*, 65, 27-31 (1997).

* cited by examiner

*Primary Examiner* — Bao Li
(74) *Attorney, Agent, or Firm* — Leydig, Voit & Mayer, Ltd.

(57) ABSTRACT

Methods for preparing cells and viruses such as poxviruses are provided herein.

32 Claims, 6 Drawing Sheets

METHODS FOR PREPARING CELLS AND VIRUSES

CROSS-REFERENCE TO RELATED APPLICATIONS

This patent application is a U.S. National Phase of International Patent Application No. PCT/US2005/040170, filed Nov. 4, 2005, which claims the benefit of priority to U.S. Provisional Patent Application No. 60/625,321, filed Nov. 5, 2004, the contents of which are hereby incorporated by reference in their entirety.

TECHNICAL FIELD

This invention relates to methods for preparing cells and viruses, and more particularly to methods for preparing poxviruses.

BACKGROUND

Worldwide elimination of smallpox by vaccination with orthopox viruses such as vaccinia has validated the safety and efficacy of poxvirus vaccines. Today, poxviruses have a wide range of applications, in part because these viruses contain large genomes that can accommodate insertion of foreign DNA. For example, the vaccinia virus genome can tolerate insertions of up to 25,000 base pairs of foreign DNA (Smith and Moss, *BioTechniques*, 25(1):21-28, 1983). Thus, poxviruses are used to stimulate responses not only to poxviral antigens, but also to heterologous viral, bacterial, or tumor antigens with numerous prophylactic and therapeutic indications. In addition, poxviruses can be used to deliver any therapeutic DNA, such as a transgene encoding a therapeutic protein (e.g., a cytokine), into a subject. Production of virus stocks in vitro is preferable to propagation in animal hosts from a safety standpoint (Hruby, *Clin. Microbio.*, 3(2): 153-170, 1990). However, large-scale commercial production can be hampered by the limited cell types such as primary cells to support virus production in vitro. Optimizing virus yield and quality in cell culture-based manufacturing methods will increase the commercial feasibility of therapeutic viral vectors.

SUMMARY

The invention is based on the discovery that specific modification of viral production processes can lead to surprisingly dramatic increases in yield or robustness. One such change is the removal of centrifugation from the cell preparation steps prior to virus infection.

In one aspect, the invention features a method for preparing cells competent for virus replication from a biological tissue. The method includes, for example: (a) providing a biological tissue comprising primary cells susceptible to infection with a virus that replicates in the cells; (b) exposing the tissue to a solution comprising a protease, thereby causing cells of the tissue to be dissociated and be released into the solution; (c) inactivating the protease in the solution; and (d) preparing the released cells for infection with the virus; and (e) infecting the released cells with the virus, wherein the released cells are not centrifuged at any point prior to infection with the virus.

In one embodiment, the biological tissue provided in step (a) includes avian embryo tissue, e.g., chicken embryo tissue.

In one embodiment, the protease is inactivated by addition of a solution including serum. Sufficient serum can be added to the solution in step (c) to produce a concentration of less than 10%, 8%, 6%, or 5.5% serum in the solution.

In one embodiment, the protease is trypsin (e.g., trypsin from an animal source, or recombinant trypsin, e.g., from a non-mammalian microbial source such as bacteria). Trypsin can be present in the solution of (b) at a concentration of 0.25% g/L, 0.16% g/L or less. In one embodiment, the trypsin is inactivated in step (c) by addition of a trypsin inhibitor to the solution, e.g., soybean trypsin inhibitor.

Step (b) can include agitation of the solution containing the tissue, e.g., agitation in an orbital shaker running at a speed of at least 95, 100, 120, 140, 160, 180, 200, 220, or 240 revolutions per minute (rpm).

Step (d) can include passing the solution containing the released cells through a filter.

The avian embryo tissue can be obtained from one or more embryos (e.g., 50, 100, 150 or more embryos).

The cells produced by the method can be competent for infection with a poxvirus, e.g., vaccinia virus, or an avipox virus such as fowlpox virus or canarypox virus.

In various embodiments, the cells in step (e) are infected in a medium in which the concentration of serum is 0.1%, 0.05%, 0.02%, 0.01%, or less. In one embodiment, the cells in step (e) are infected in the absence of serum.

The method can further include (f) incubating the infected cells in a culture medium under conditions in which virus replication occurs in the cells, and, optionally, (g) isolating virus from the incubated infected cells. In one embodiment, the virus is isolated from the cells in step (g) without the use of centrifugation. The method can also include (h) isolating virus as from the medium, or from the cells and medium, e.g., using filtration.

In one embodiment, the released cells are infected with virus in step (e) and added to a container for incubation at the same time (e.g., the cells are infected at the time of plating). In one embodiment, the cells are added to a container (e.g., plated) prior to infection (e.g., one hour, two hours, three hours, or one day prior to infection).

In another aspect, the invention features a method for producing virus in vitro. The method includes, for example: providing cells permissive for replication of a virus; infecting the cells with the virus in vitro; incubating the cells in medium under conditions in which the virus replicates in the cells; and isolating virus from the cells and medium without the use of centrifugation.

The cells can be primary cells (e.g., embryonic cells, such as avian embryonic cells). The cells can be cells of a cell line (e.g., monkey kidney cells, e.g., Vero cells).

The virus can be a poxvirus, e.g., vaccinia or an avipox such as fowlpox or canarypox.

In one embodiment, the cells are prepared from a biological tissue e.g., an avian embryo tissue, and have not been centrifuged.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Yield and robustness of virus produced in vitro are critically dependent on cell type and culture conditions. Classical methods for the production of poxviruses such as fowlpox rely on propagation of the virus in the chorioallantoic membranes of avian embryos or in primary chicken embryo cells. Preparation of chicken embryo cells for virus production requires dissociation of the chicken embryo to release cells, typically by digestion of the embryo with a protease such as trypsin. We have found that the methods by which cells (e.g., primary cells obtained from tissue) are processed impacts the yield and quality of virus produced in the cells. We have also found that the methods by which virus is harvested from cells in vitro impacts yield and quality.

A novel exemplary method for the preparation of chicken embryo cells is described in Example 1, below. Briefly, cells prepared according to this novel method are obtained from a chicken embryo that is digested in a protease such as trypsin, where the trypsin is neutralized by addition of serum. Typically, one would centrifuge the cells after this step and prior to infection to remove the medium containing any residual trypsin. We have found that cells can be prepared from embryos without the use of centrifugation (e.g., without centrifugation at any step) prior to infection. Not only do cells prepared in this manner support high levels of viral replication, but the methods are suitable for efficient, large-scale virus production. Accordingly, the invention features methods for preparing cells from a biological tissue for virus infection in which the cells are not centrifuged between the step in which the cells are isolated (e.g., released from a tissue) and infected with virus.

We show that other features of cell preparation impact virus production. One such feature is the mode by which cells are dissociated from tissue in the presence of trypsin. Dissociation by agitation on an orbital shaker at high speed (e.g., from 75-300 revolutions per minute (rpm), e.g., 100-200 rpm, e.g., 130-150 rpm) results in recovery of cells that support higher levels of virus propagation than cells produced by agitation at lower speeds.

We have also found that harvesting virus from cells without the use of centrifugation steps facilitates recovery of higher yields of more robust virus. For example, we isolated poxvirus from infected cells by incubation in a hypotonic solution (1 mM Tris pH 9.0) and filtration of the disrupted cell mixture. Yields of virus obtained by this method were comparable to, or greater than, yields obtained by a standard method employing centrifugation. Furthermore, virus can be harvested more efficiently (and on a larger scale) without the need for centrifugation steps.

Finally, we have also discovered that poxvirus can be propagated in the presence of low concentrations of serum and that this does not impact virus yield (and may, in fact, enhance virus yield). We have produced poxvirus from cells in the presence of approximately 0.01% serum for the total incubation time of 4-5 days and found no adverse effect on yield.

Preparation of Cells from Biological Tissues

The methods described herein can be used to prepare cells from any biological tissue (e.g., any solid tissue from an organism). In various embodiments, cells will be prepared from embryonic tissue (e.g., avian embryonic tissue, or mammalian embryonic tissue, e.g., murine, primate, bovine, ovine, feline, canine, or porcine tissue). Cells can also be prepared from fetal, post-natal, and adult tissues. The choice of tissue will depend on the type of virus to be produced. Certain viruses grow most efficiently in specific cell types (e.g., lung, renal, hepatic, muscle, dermal, epidermal, neuronal, thymic, or cardiac tissues).

Cells can be released from tissues by a variety of means. Proteases are typically used for this step. Trypsin, collagenase, dispase, ACCUTASE® (Innovative Cell Technologies, Inc.) and pronase are examples of proteases that can be used to digest tissues. Proteases from a mammalian (e.g., porcine or bovine) or non-mammalian (e.g., plant, fungal or microbial) source may be used. Recombinant proteases (e.g., recombinant trypsin) produced in non-mammalian cells are commercially available. The concentration of protease used to release the cells is typically in the range of 0.5%-0.1% g/L, although the optimal concentration will depend on the tissue and the particular protease selected. One can determine an optimal concentration by comparing cell yields in the presence of varying concentrations of protease. Ethylenediaminetetraacetic acid (EDTA) can be used in addition to, or in place of protease to release cells from a tissue.

The mixture of tissue and protease (typically in a buffered solution) can be incubated with agitation to promote release of cells. We have found that rapid agitation (e.g., agitation on an orbital shaker at speeds of 75-300 rpm) increases cell yields. Alternatively, a stir bar (e.g., a magnetic stir bar) placed in the container with the mixture is used to promote release of the cells.

Proteases used to release cells from tissue are inactivated (e.g., partially inactivated, or completely inactivated), e.g., by the addition of proteins that include a specific inhibitor of the protease, and/or are rich in amino acids sequences recognized by the protease (e.g., serine-rich, for inactivation of serine proteases such as trypsin). Animal serum (e.g., fetal or neonatal bovine serum) is suitable for protease inactivation. Protein derived from non-animal sources (e.g., fungal, bacterial, or plant protein extracts, or purified proteins derived therefrom) can also be used. In various embodiments, the protein is added to a final concentration of less than 2%, 1.5%, 1.25%, 1%, 0.75%, 0.5%, 0.25%, 0.125%, 0.06%, 0.03%, or 0.01% (w/v). In general, the protein is added in an amount sufficient to inactivate at least 50%, 60%, 70%, 80%, 90%, 95%, or 99% of the protease. Medium is added to the cell/tissue suspension, and the released cells are separated from the non-dissociated tissue components (e.g., by filtration). Dilution of protease by the addition of medium further reduces proteolytic activity in the suspension. Of note, centrifugation is not employed to remove the protease in the solution, thereby lessening the stress on the cells and increasing efficiency of the process.

Virus Production

The methods described herein are applicable to the in vitro production of any virus, e.g., a poxvirus, orthomyxovirus, paramyxovirus, reovirus, picornavirus, flavivirus, arenavirus, herpesvirus, coronavirus, or an adenovirus. More specifically, the virus produced can be vaccinia virus and variola, fowlpox virus, canarypox virus, cowpox virus, influenza virus, tick-borne encephalitis virus (TBE), poliovirus, Hepatitis A virus, Ross River virus, Yellow fever virus, West nile virus, Japanese encephalitis virus, rubella virus, hepatitis C virus (HCV), mumps virus, measles virus, respiratory syncytial virus (RSV), herpes simplex virus (HSV), cytomegalovirus (CMV), Epstein-Barr virus (EBV), rotavirus, Severe Acute Respiratory Syndrome-Coronavirus (SARS-CoV), or foot and mouth disease virus (FMDV).

Viruses infect cells in vitro under conditions in which virus replication occurs in the cells. Optimal temperature, duration, and medium for infection can be determined empirically. Surprisingly, we have found that primary cells prepared from tissue according to methods described herein (e.g., methods in which the cells are not centrifuged at any point prior to infection) support high levels of virus replication across a wider range of infection times as compared to cells prepared by conventional means. Cells can be infected and incubated in the absence of serum or any other exogenous protein, or in minimal concentrations of serum or exogenous protein (e.g., at concentrations of less than 1%, 0.05%, 0.02%, 0.01% serum).

Virus can be harvested from cells by a variety of means. Viruses shed into the medium can be collected by aspirating the medium. Cell-associated virus can be obtained by lysing cells (e.g., by hypotonic lysis, freeze/thaw lysis, microfluidization, or sonication). In one embodiment, virus is harvested from cells without the use of any centrifugation steps. Viruses can be harvested from adherent cells by removing medium from the cells by aspiration and lysing the cells in a hypotonic solution. Cell debris is separated from virus and medium by filtration (e.g., depth filtration), host cell genomic DNA in the virus/medium obtained after filtration is digested by addition of a nuclease, and virus is further purified and concentrated by a filtration system that retains virus and allows flow through of the medium, and nucleic acid debris, nuclease, and other soluble protein contaminants. Conventional means may also be used to harvest virus. For example, virus may be purified by centrifugation through a sucrose cushion.

EXAMPLES

Example 1

Preparation of Chicken Embryo Cells

The following procedure can be used to prepare chicken embryo cells from a batch of 100 eggs or fewer. Pour 800 ml sterile phosphate buffered saline (PBS) into a 3 L polycarbonate Erlenmeyer baffled flask in a biological safety cabinet (BSC). Close cap. Thoroughly spray the fat tops of the eggs with STERI-PEROX® (Veltek Associates, Malvern Pa.) and leave the eggs in BSC to dry for a minimum of 10 minutes. Process three eggs at a time by aseptically removing the top of each egg with an egg cutter and transferring the embryos to the polycarbonate Erlenmeyer baffled flask. After all embryos are harvested, close the flask cap. Wash the embryos by swirling the flask and aspirate the PBS. Add 800 ml PBS, rewash by gentle swirling, and aspirate the PBS. Repeat three more times for a total of five washes, aspirating the PBS after the last wash.

Add 800 ml of recombinant trypsin, TrypLE™ Select (Gibco, Cat. # 12563-029) to the flask. Close and gently swirl the flask. Place the flask on an orbital shaker in a warm room (37±2° C.) and shake at approximately 140 revolutions per minute (rpm) for 60±5 minutes. After trypsinization, transfer the flask to the BSC. Add 100 ml of fetal bovine serum (FBS) to the flask and gently swirl. Add glutamine (4 mM final concentration) to a 1 L bottle of virus production-serum free medium (VP-SFM) (Gibco). Add 800 ml of the VP-SFM/glutamine to the flask of embryos. Close the flask and gently swirl.

Assemble two sterile polyester mesh-wrapped funnels and polycarbonate Erlenmeyer baffled flasks for filtration of the cell suspension. Pour approximately 900 ml of the cell suspension from the flask through the first autoclaved polyester mesh-wrapped funnel, into the polycarbonate Erlenmeyer baffled flask. Pour the remaining content through the second funnel. Allow the filtration to continue for 5 minutes. Discard the embryonic body parts removed by filtration. Place the flask containing the chicken embryo cells at 2-8° C. Cells may be stored for up to 24 hours prior to use.

Example 2

Production of Purified Vaccinia Virus

Add L-glutamine to each of four 1 L roller bottles of VP-SFM under sterile conditions. Remove a suspension of chicken embryo cells (prepared as described in Example 1, above) from the refrigerator. Add cells ($2.4 \times 10^8$ cells per 1 L roller bottle) to each of the four roller bottles and invert to mix. Thaw a vaccinia virus stock, vortex 1-2 seconds. Prepare a dilution of virus stock in 20 ml of VP-SFM/glutamine, vortex, and add 1 ml of the virus suspension to each of the 4 roller bottles containing the cells. Virus is added at an amount to provide 0.1 plaque forming units (pfu) per cell. After VP-SFM/glutamine-virus-cells mixtures are made, pour 150-200 ml from each bottle into a new 1 L bottle (there will be 20 roller bottles total after this step, as each mixture will be divided among 5 bottles).

Connect sparge gas tubing with 0.2 μm inline filter to sparge gas source (10% $CO_2$/20% $O_2$/balance $N_2$). Attach a 10 ml sterile pipette to sparge gas tubing. Open sparge gas valve and sparge each roller bottle for approximately 15 seconds. Close valve and tighten roller bottle caps. Place roller bottles on roller rack in 34.5±1.5° C. warm room. Roller racks are set at a constant speed of ⅛-1/10 rpm. Incubate for 92-100 hours.

Remove infection medium from each roller bottle under sterile conditions by tilting it and aspirating the medium. Add 40 ml of 1 mM Tris, pH 9.0, to each infected roller bottle. Cap the roller bottles and return them to the roller rack for 30-40 minutes. Remove the roller bottles and swirl to dislodge cells from the walls. Remove the crude harvest by aspiration.

Virus is isolated from the crude harvest by depth filtration through a 1.2 μm 5 ft² polypropylene filter (Satorius Sartopure). Additional virus can be recovered by washing the filter with 1 mM Tris pH 9 to wash out virus in the tubing and filter. Filtered virus solution is drained into a sterile bag.

Next, the filtered virus solution is treated with a nuclease, benzonase, to remove host cell nucleic acids. Pump benzonase solution through a filter and into the bag containing the filtered virus solution, to achieve a final benzonase concentration of 100 units/ml. Mix the contents thoroughly for approximately 30 seconds. Leave the bag at room temperature for 20-24 hours.

Next, tangential flow filtration (TFF) through a 50 nM membrane (Spectrum Labs) is used to purify and concentrate virus. DiaFilter the virus solution under pressure with the pump set to 300 ml/minute at initiation of filtration, gradually increasing the flow rate to 1650 ml/minute. Diafiltration can concentrate the virus 20-fold. The volume prior to diafiltration for a preparation of 100 embryos is typically 4 L. Thus, the volume after diafiltration is approximately 200 mL.

Add sterile glycerol to the purified virus stock to a final concentration of 10% (v/v). Store at −70° C.

Purified fowlpox virus can also be prepared as described in this example, except that fowlpox virus is typically incubated with cells at 37±2° C. (rather than 34.5±1.5° C. for vaccinia).

Example 3

Comparisons of Variables in Virus Production Methods

The effects on virus production of agitation speed during preparation of chicken embryo cells and reagents for inactivating trypsin were evaluated. The overall method for preparing chicken and virus in the absence of centrifugation, as described in Examples 1 and 2, was compared to a standard method that employs centrifugation steps.

First, chicken embryo cells were prepared as described in Example 1, except that one batch was prepared with agitation at 95 rpm and another batch was prepared with agitation at 140 rpm. Trypsinization was halted by addition of either FBS or soybean trypsin inhibitor (SBTI). Purified vaccinia virus was prepared with each set of chicken embryo cells.

For additional comparison, purified vaccinia virus was also produced according to a standard method, P2, which has the following differences from the methods described in Examples 1 and 2. Chicken eggs were sanitized with Decon-Ahol® (Veltek Associates, Malvern, Pa.). Embryos (25/batch) were digested in a crystallizing dish with a stir bar rotating at 200 rpm (rather than with agitation on a shaker). The suspension was filtered through cheese cloth and the filtered suspension was centrifuged to isolate chicken embryo cells. Chicken embryo cells were infected with virus in Dulbecco's Modified Eagle's Medium (DME) with 2% FBS and dispensed into roller bottles. Cells and virus were incubated for 4 days at 34.5±1.5° C. for vaccinia and 37±2° C. for fowlpox. Infected cells were harvested by centrifugation. The cell pellets were resuspended in 1 mM Tris, pH 9.0. The mixture was centrifuged and the supernatant was collected. The cell pellet was resuspended in 1 mM Tris, pH 9.0, and centrifuged again, and supernatants were pooled to produce clarified bulk virus stock. Virus was purified and concentrated by centrifugation through a 20% sucrose cushion. Virus pellet was resuspended in PBS/10% glycerol and stored at −70° C. or colder.

Figure 1:
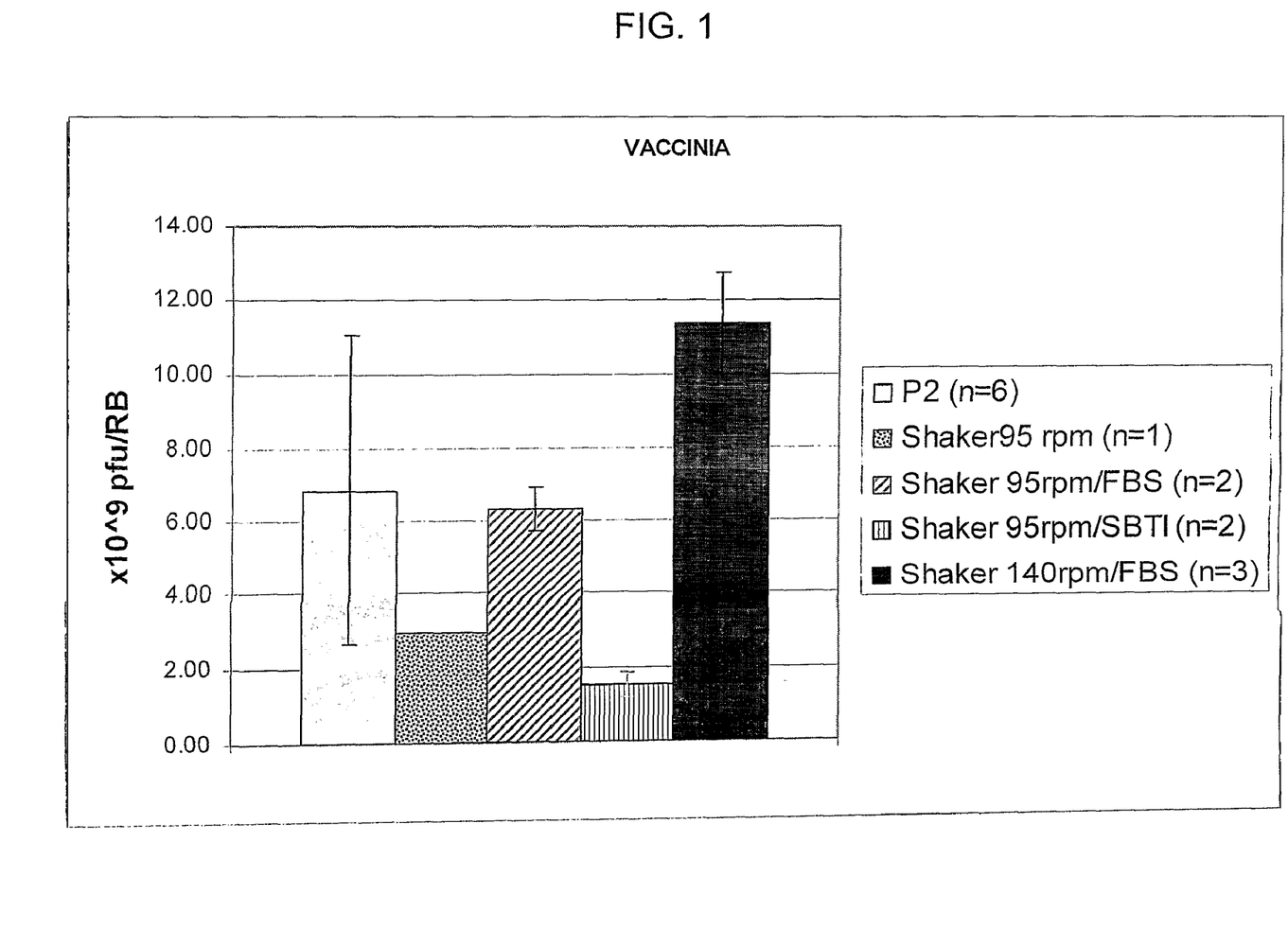
FIG. 1 is a graph depicting the results in which efficiency of virus production by several different methods was examined. Each bar represents plaque forming units (pfu) of vaccinia virus obtained per roller bottle (RB) for virus obtained from cells according to a standard method (P2) or a novel method (all "Shaker" samples) in which the speed of agitation of cells during cell preparation was varied (95 revolutions per minute vs. 140 revolutions per minute) and in which the method of neutralization of trypsin was varied (no neutralization; neutralization by fetal bovine serum (FBS); or neutralization by soybean trypsin inhibitor (SBTI)).

Virus was produced in cells prepared according to each method and pfu yields per roller bottle were compared. Procedures for determining pfu, including plaque assays in agarose, are well known. See, e.g., Moss et al., Unit 16, Expression of proteins in mammalian cells using vaccinia viral vectors, In: Current Protocols in Molecular Biology, John Wiley & Sons, Inc., 1998. The results in FIG. 1 show that the use of 140 rpm agitation and FBS for trypsin neutralization yielded cells that supported higher levels of virus production as compared to cells prepared with 95 rpm agitation and SBTI neutralization. Yields from cells prepared according to the standard method, P2, were comparable to yields from cells prepared with 140 rpm/FBS neutralization.

Chicken embryo cells cell yields per embryo for when the standard method is used are comparable to the method in which 140 rpm agitation is used (data not shown).

Figure 2:
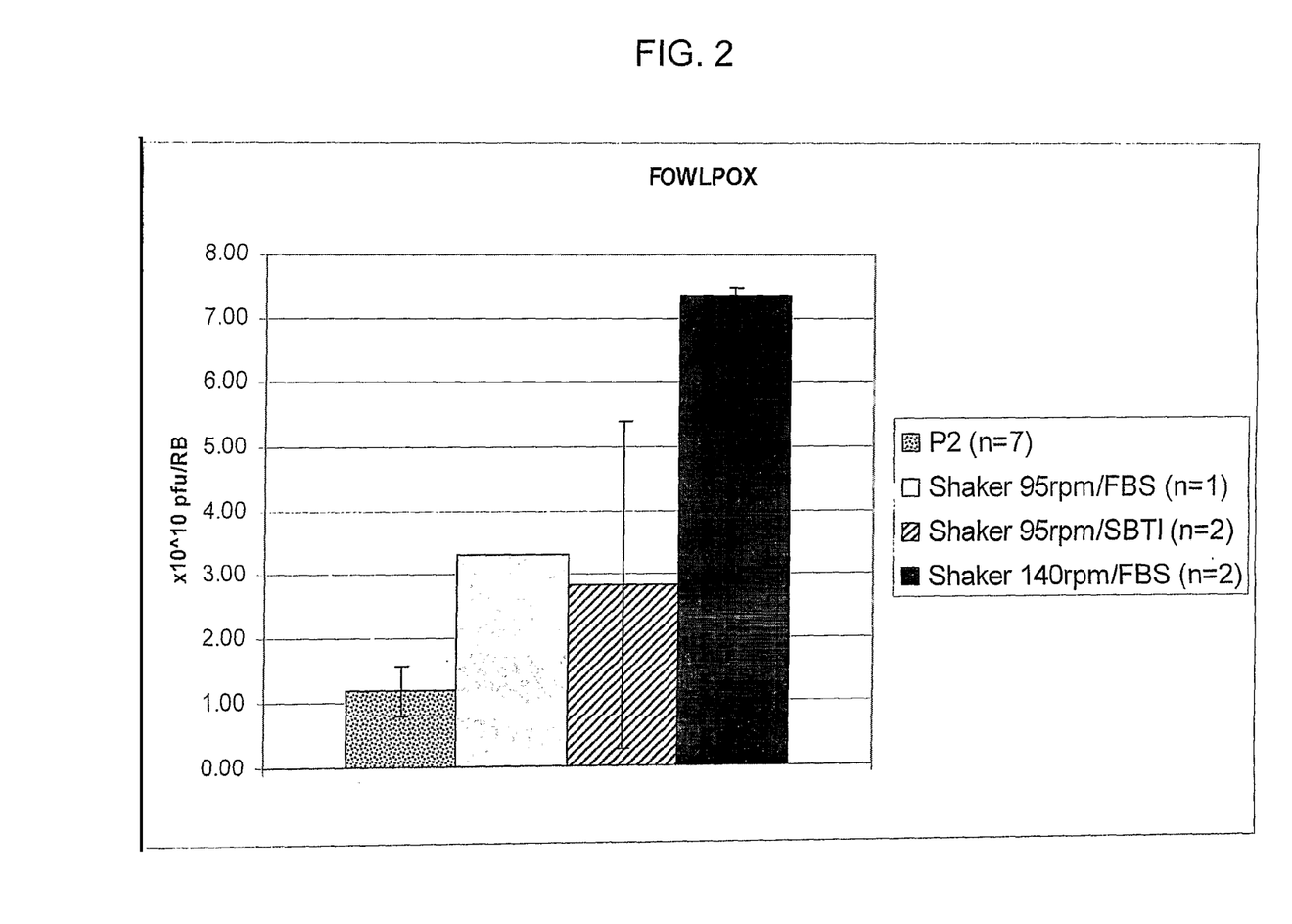
FIG. 2 is a graph depicting the results in which efficiency of virus production by several different methods was examined. Each bar represents plaque forming units (pfu) of fowlpox virus obtained per roller bottle (RB) for virus obtained from cells according to a standard method (P2) or a novel method (all "Shaker" samples) in which the speed of agitation of cells during cell preparation was varied (95 revolutions per minute vs. 140 revolutions per minute) and in which the method of neutralization of trypsin was varied (by fetal bovine serum (FBS) or by soybean trypsin inhibitor (SBTI)).
Figure 3A:
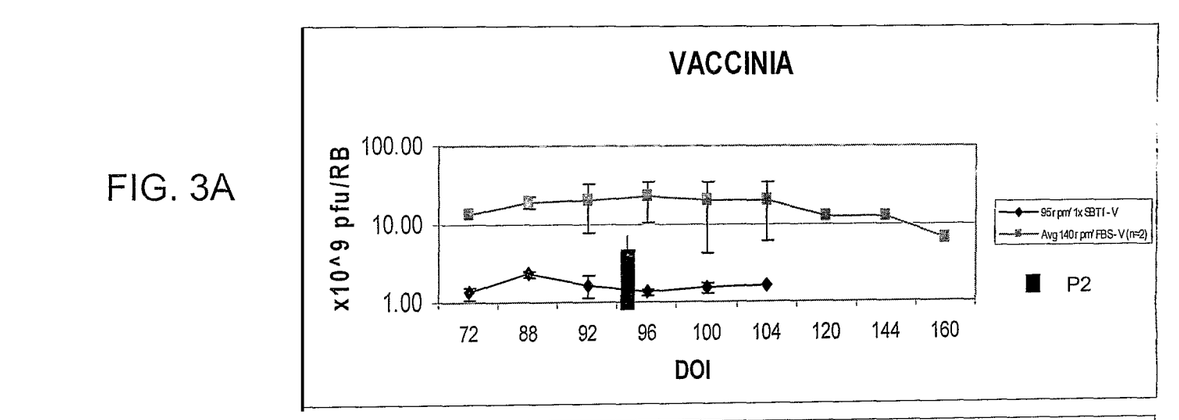
FIGS. 3A and 3B are a set of graphs depicting levels of vaccinia (FIG. 3A) and fowlpox (FIG. 3B) production over a range of hours. "DOI" refers to duration of infection.
Figure 3B:
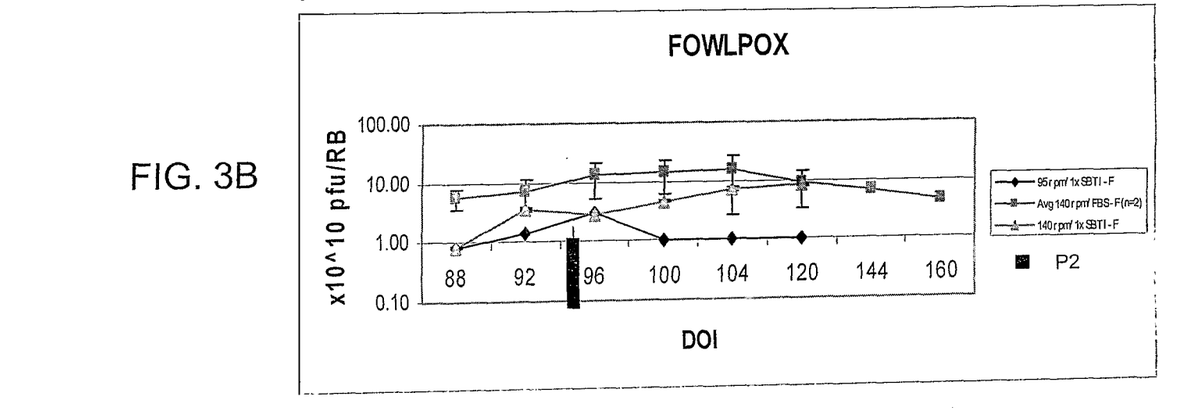
Figure 4A:
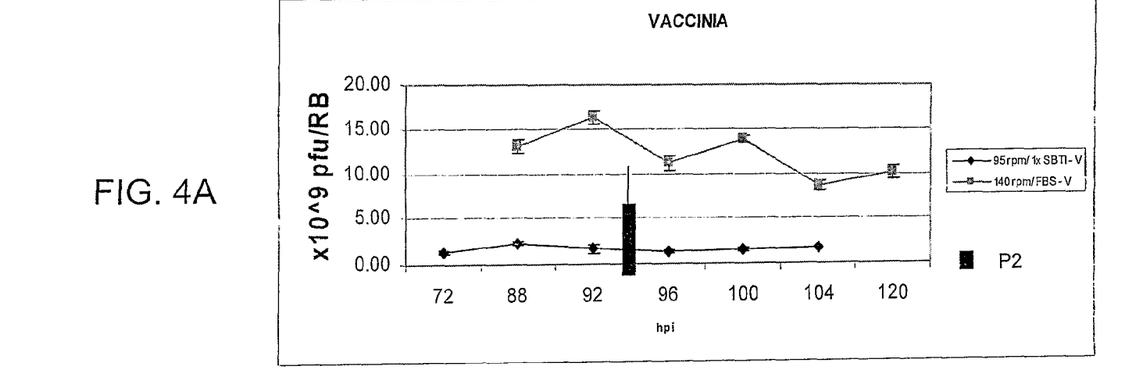
FIGS. 4A and 4B are a set of graphs depicting levels of vaccinia (FIG. 4A) and fowlpox (FIG. 4B) production over a range of hours.
Figure 4B:
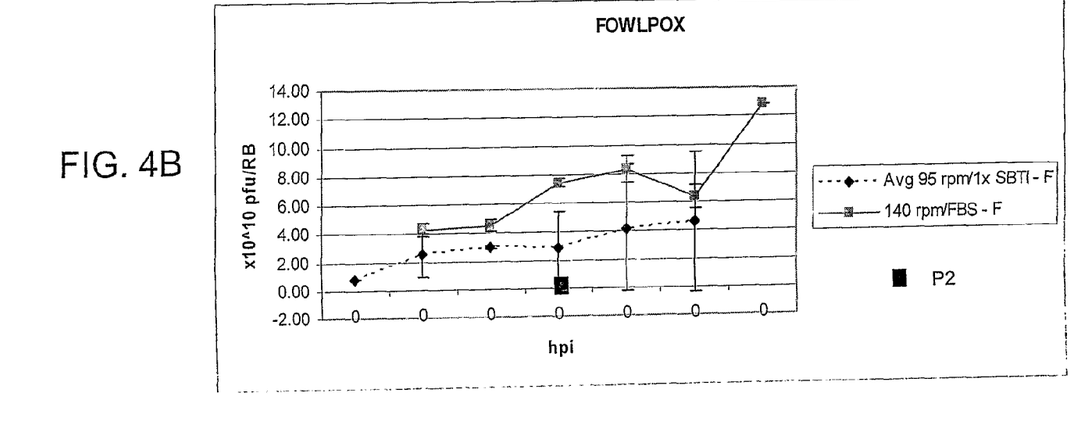

The experiment depicted in FIG. 1 was repeated with fowlpox as the infecting virus rather than vaccinia. The results are depicted in FIG. 2. As shown, cells prepared with 140 rpm agitation and FBS neutralization supported levels of virus production twice as high as methods employing 95 rpm. Surprisingly, the cells produced seven times more virus than cells produced by the standard method (P2). Thus, the methods detailed in Examples 1 and 2 produce much higher levels of fowlpox virus as compared to the standard method.

Duration of Infection and Virus Production

Next, we examined virus production over a range of hours. Vaccinia or fowlpox virus were prepared using the methods described in Examples 1 and 2, but with the following variables: cells were either harvested from tissue using agitation at 95 rpm and trypsin was neutralized by SBTI; or cells were agitated at 140 rpm and neutralized with FBS. Virus production over 72, 88, 92, 96, 100, 104, 120, 144, and 160 hours was measured. The results are shown in FIGS. 3A, 3B, 4A, and 4B. Both vaccinia and fowlpox were produced at much higher levels in cells prepared with 140 rpm agitation and FBS neutralization at nearly every time point analyzed. Furthermore, levels produced with 140 rpm agitation and FBS neutralization were much higher than that produced by method P2 at 96 hours. Surprisingly, consistently high titers of virus were observed over the range of times tested for the optimal method in these experiments (140 rpm and FBS neutralization).

Further Comparison of Shaker Speeds and Neutralization Reagents

Figure 5A:
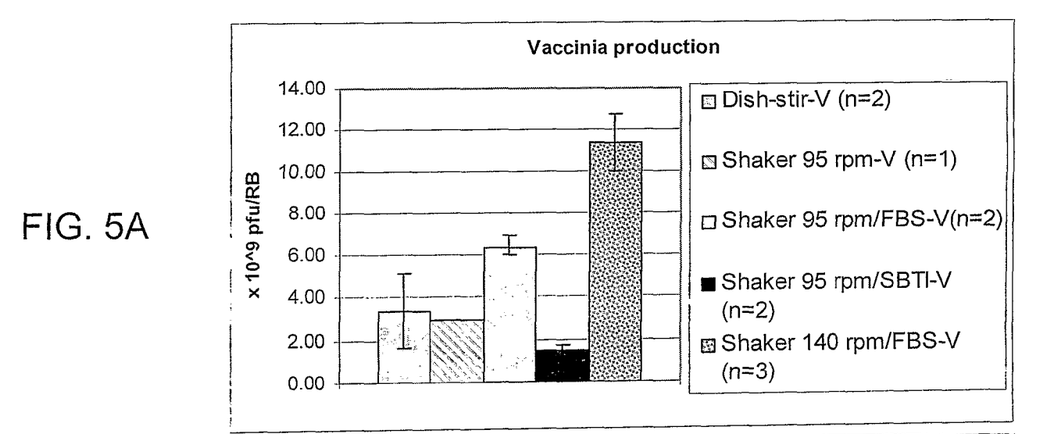
FIGS. 5A and 5B are a set of graphs depicting levels of vaccinia (FIG. 5A) and fowlpox (FIG. 5B) production under conditions in which cells were prepared using a dish-stir method, or using a method employing an orbital shaker agitating at 95 or 140 rpm, and in which trypsin was neutralized either by SBTI or FBS.
Figure 5B:
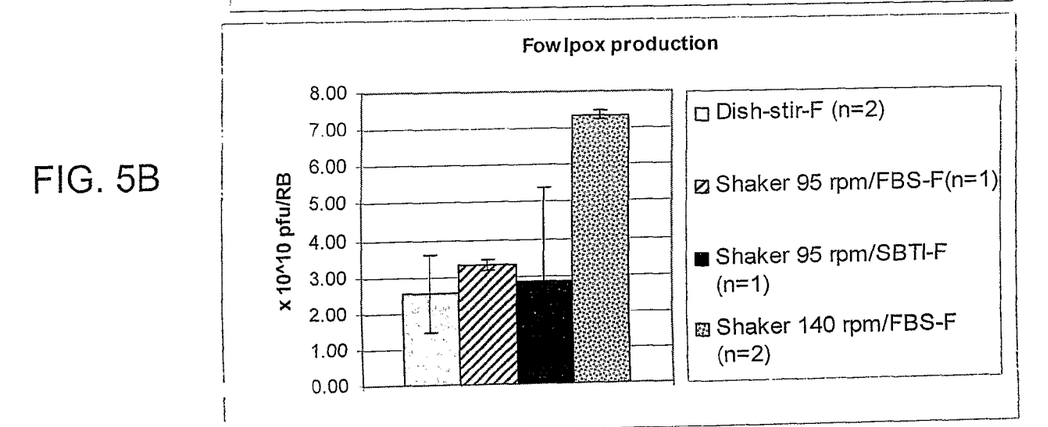

We repeated our comparison of method P2 to the methods of Examples 1 and 2 for both vaccinia and fowlpox production. We also repeated our comparison of shaker speeds (95 rpm vs. 140 rpm) and trypsin neutralization reagents (SBTI vs. FBS). The results are shown in FIGS. 5A and 5B. As shown in FIGS. 5A and 5B, the cell preparation method employing 140 rpm and FBS neutralization supported far higher levels of both vaccinia and fowlpox virus production than all other methods tested in this experiment, yielding, on average, twice as much virus as the other methods. SBTI neutralization was far less effective for preparation of cells for vaccinia infection. "Dish-stir" bars in each graph correspond to experiments performed with cells prepared by method P2, employing a stir bar to release cells from tissue.

Figure 6A:
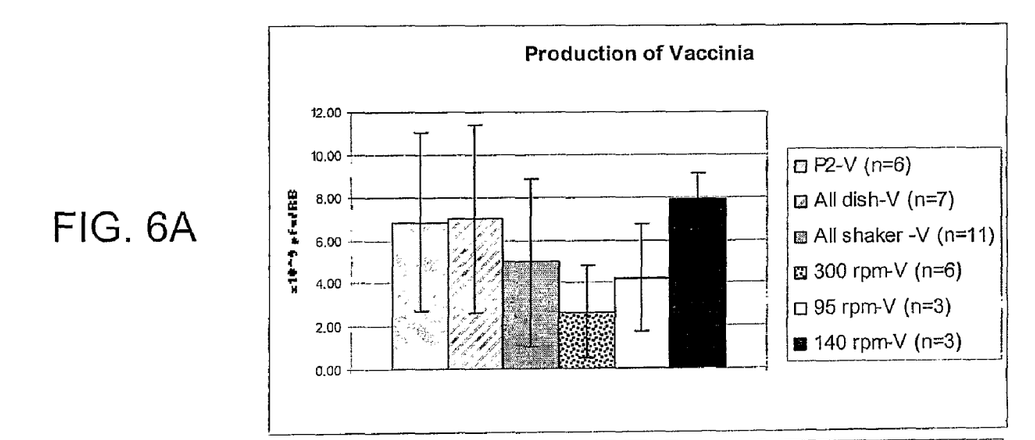
FIGS. 6A and 6B are a set of graphs depicting levels of vaccinia (FIG. 6A) and fowlpox (FIG. 6B) production under conditions in which cells were prepared using method P2, or using a method employing an orbital shaker agitating at 95, 140, or 300 rpm, and in which trypsin was neutralized either by SBTI or FBS.
Figure 6B:
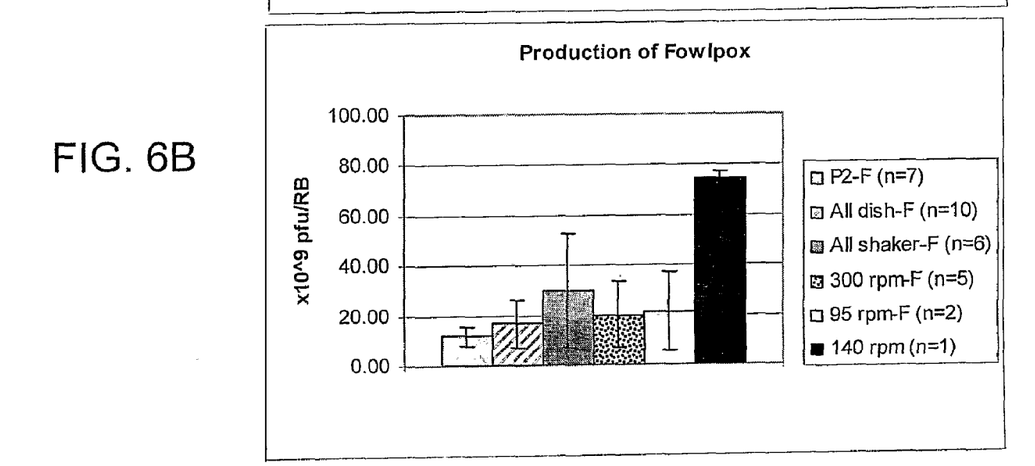

We also tested virus production in cells prepared at a wider range of shaker speeds. Cells were prepared according to method P2 and the methods of Examples 1 and 2, but wherein shaker speeds of 95, 140, or 300 rpm were used. Production of vaccinia and fowlpox in the cells was determined. As shown in FIG. 6A, cells produced at 140 rpm yielded more vaccinia virus than cells produced at either 95 or 300 rpm. Yields of vaccinia virus from cells prepared by method P2 were comparable to yields for the cells produced at 140 rpm. As shown in FIG. 6B, cells produced at 140 rpm yielded more fowlpox than all other methods tested in that experiment.

Cells made under different conditions (either with method P2, in a dish, or with the method of Examples 1 and 2) were pooled prior to infection. The results for these cells are listed as "all dish" and "all shaker", respectively, on each graph in FIGS. 6A and 6B. The pooled "dish" samples and "shaker" samples produced comparable levels of vaccinia virus. However, these pooled samples supported far less fowlpox virus production.

A number of embodiments of the invention have been described. Nevertheless, it will be understood that various modifications may be made without departing from the spirit and scope of the invention. Accordingly, other embodiments are within the scope of the following claims.

What is claimed is:

1. A method for preparing cells competent for poxvirus replication from a biological tissue, the method comprising:
    (a) providing a biological tissue comprising avian primary cells susceptible to infection with a poxvirus that replicates in the cells;
    (b) exposing the biological tissue to a solution comprising a protease, and agitating the biological tissue in an orbital shaker running at a speed of at least 95 revolutions per minute (rpm), thereby causing cells of the biological tissue to be dissociated and be released into the solution;
    (c) inactivating the protease in the solution;
    (d) separating the released cells from the non-dissociated tissue components; and
    (e) infecting the released cells with the poxvirus, wherein the released cells are not centrifuged at any point prior to infection with the poxvirus.

2. The method of claim 1, wherein the biological tissue provided in (a) comprises avian embryo tissue.

3. The method of claim 2, wherein the avian embryo tissue is chicken embryo tissue.

4. The method of claim 1, wherein the protease is trypsin.

5. The method of claim 4, wherein trypsin is present in the solution of (b) at a concentration of 0.25% g/L or less.

6. The method of claim 1, wherein the protease is inactivated by addition of a solution comprising serum.

7. The method of claim 6, wherein sufficient serum is added to the solution in (c) to produce a concentration of less than 10% serum in the solution.

8. The method of claim 4, wherein the trypsin is inactivated in (c) by addition of a trypsin inhibitor to the solution.

9. The method of claim 7, wherein the trypsin inhibitor is soybean trypsin inhibitor.

10. The method of claim 1, wherein (d) comprises passing the solution containing the released cells through a filter.

11. The method of claim 2, wherein the avian embryo tissue is obtained from one or more embryos.

12. The method of claim 4, wherein the trypsin is recombinant.

13. The method of claim 12, wherein the recombinant trypsin is produced in a non-mammalian cell.

14. The method of claim 13, wherein the recombinant trypsin is produced in a bacterial cell.

15. The method of claim 1, wherein the poxvirus is a vaccinia virus or an avipox virus.

16. The method of claim 15, wherein the avipox virus is a fowlpox virus or canarypox virus.

17. The method of claim 1, wherein the cells in (e) are infected in a medium in which the concentration of serum is 0.1% or less.

18. The method of claim 1, further comprising (f) incubating the infected cells in a culture medium under conditions in which poxvirus replication occurs in the cells.

19. The method of claim 18, further comprising (g) isolating poxvirus from the incubated infected cells.

20. The method of claim 19, wherein the poxvirus is isolated from the cells in (g) without the use of centrifugation.

21. The method of claim 19, further comprising (h) isolating poxvirus from the medium.

22. The method of claim 21, wherein the poxvirus is isolated using filtration.

23. The method of claim 19, wherein the poxvirus is isolated from the cells and the medium using filtration.

24. The method of claim 1, wherein the released cells are infected with poxvirus in (e) and added to a container for incubation at the same time.

25. The method of claim 1, wherein the agitation runs at a speed of 130-150 revolutions per minute (rpm), and wherein the protease is inactivated by addition of a solution comprising serum.

26. The method of claim 25, wherein the poxvirus is vaccinia or fowlpox virus.

27. A method for producing poxvirus in vitro, the method comprising:

(a) providing a biological tissue comprising avian primary cells susceptible to infection with a poxvirus that replicates in the cells;

(b) exposing the biological tissue to a solution comprising a protease, and agitating the biological tissue in an orbital shaker running at a speed of at least 95 revolutions per minute (rpm), thereby causing cells of the biological tissue to be dissociated and be released into the solution;

(c) inactivating the protease in the solution;

(d) separating the released cells from the non-dissociated tissue components;

(e) infecting the released cells with the poxvirus, wherein the released cells are not centrifuged at any point prior to infection with the poxvirus;

(f) incubating the cells in medium under condition in which the poxvirus replicates in the cells; and (g) isolating poxvirus from the cells and medium without the use of centrifugation.

28. The method of claim 27, wherein the cells are avian embryonic cells.

29. The method of claim 28, wherein the cells are avian embryonic dermal cells.

30. The method of claim 27, wherein the poxvirus is a vaccinia virus or an avipox virus.

31. The method of claim 30, wherein the avipox virus is a fowlpox or a canarypox.

32. The method of claim 27, wherein the cells are prepared from avian embryo tissue.

* * * * *